(12) United States Patent
Thakur et al.

(10) Patent No.: US 12,369,838 B2
(45) Date of Patent: Jul. 29, 2025

(54) SYSTEMS AND METHODS FOR PREDICTING ATRIAL ARRHYTHMIA

(71) Applicant: Cardiac Pacemakers, Inc., St. Paul, MN (US)

(72) Inventors: Pramodsingh Hirasingh Thakur, Woodbury, MN (US); Rezwan Ahmed, Arden Hills, MN (US); Stephen B. Ruble, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 200 days.

(21) Appl. No.: 18/112,040

(22) Filed: Feb. 21, 2023

(65) Prior Publication Data
US 2023/0200710 A1    Jun. 29, 2023

Related U.S. Application Data

(63) Continuation of application No. 16/821,332, filed on Mar. 17, 2020, now Pat. No. 11,602,298.
(Continued)

(51) Int. Cl.
*G16H 10/60* (2018.01)
*A61B 5/00* (2006.01)
(Continued)

(52) U.S. Cl.
CPC ............ *A61B 5/361* (2021.01); *A61B 5/1135* (2013.01); *A61B 5/74* (2013.01); *G16H 10/60* (2018.01); *G16H 50/30* (2018.01)

(58) Field of Classification Search
CPC ................................ G16H 10/60; G16H 50/30
(Continued)

(56) References Cited

U.S. PATENT DOCUMENTS

| 5,437,285 A | 8/1995 | Verrier et al. |
| 11,039,779 B2 * | 6/2021 | Thakur .............. A61B 5/02427 |

(Continued)

FOREIGN PATENT DOCUMENTS

| CN | 103517734 A | 1/2014 |
| CN | 107408144 A | 11/2017 |

(Continued)

OTHER PUBLICATIONS

U.S. Appl. No. 16/821,332, filed Mar. 17, 2020, Systems and Methods for Predicting Atrial Arrhythmia.
(Continued)

*Primary Examiner* — Michael Tomaszewski
(74) *Attorney, Agent, or Firm* — Schwegman Lundberg & Woessner, P.A.

(57) ABSTRACT

Systems and methods for assessing a cardiac arrhythmia risk of a patient, such as a risk for developing atrial fibrillation, are disclosed. An exemplary medical-device system includes a risk stratifier circuit configured to, in an absence of prior and present atrial arrhythmia, determine a composite risk of the patient developing a future atrial arrhythmia using a trained machine-learning model and a plurality of features of physiological information sensed from the patient and an arrhythmia monitor circuit configured to adjust an arrhythmia monitoring parameter based at least in part on the composite risk and to detect an atrial arrhythmia event using the adjusted arrhythmia monitoring parameter.

20 Claims, 6 Drawing Sheets

Related U.S. Application Data

(60) Provisional application No. 62/820,132, filed on Mar. 18, 2019.

(51) Int. Cl.
  *A61B 5/113* (2006.01)
  *A61B 5/361* (2021.01)
  *G16H 50/30* (2018.01)

(58) Field of Classification Search
  USPC .......................................... 600/483; 705/2–3
  See application file for complete search history.

(56) References Cited

U.S. PATENT DOCUMENTS

| | | | |
|---|---|---|---|
| 11,602,298 B2* | 3/2023 | Thakur | A61B 5/361 |
| 2006/0116594 A1* | 6/2006 | Zhang | A61B 5/349 |
| | | | 600/515 |
| 2009/0177102 A1 | 7/2009 | Schneider et al. | |
| 2011/0106200 A1 | 5/2011 | Ziegler | |
| 2011/0137193 A1 | 6/2011 | Ghanem et al. | |
| 2011/0301479 A1* | 12/2011 | Ghanem | A61N 1/3925 |
| | | | 600/515 |
| 2011/0301480 A1 | 12/2011 | Ghanem | |
| 2015/0157273 A1 | 6/2015 | An et al. | |
| 2015/0342466 A1 | 12/2015 | Thakur et al. | |
| 2016/0331247 A1 | 11/2016 | Albert | |
| 2017/0281095 A1* | 10/2017 | An | A61B 5/08 |
| 2018/0104502 A1* | 4/2018 | Perschbacher | A61B 5/361 |
| 2018/0256059 A1* | 9/2018 | Perschbacher | A61B 5/7232 |
| 2019/0343415 A1* | 11/2019 | Saha | A61N 1/36514 |
| 2020/0178829 A1* | 6/2020 | Perschbacher | A61B 5/33 |
| 2020/0297230 A1* | 9/2020 | Thakur | A61B 5/08 |
| 2021/0076960 A1* | 3/2021 | Fornwalt | A61B 5/282 |
| 2023/0200710 A1* | 6/2023 | Thakur | A61B 5/08 |
| | | | 600/483 |

FOREIGN PATENT DOCUMENTS

| | | | |
|---|---|---|---|
| CN | 108471968 A | | 8/2018 |
| CN | 109350022 A | | 2/2019 |
| CN | 113891677 A | | 1/2022 |
| CN | 113891677 B | | 8/2024 |
| EP | 2237836 A1 | | 10/2010 |
| WO | WO-2020190922 A1 | | 9/2020 |
| WO | WO-2022195139 A1 * | | 9/2022 |

OTHER PUBLICATIONS

"U.S. Appl. No. 16/821,332, Non Final Office Action mailed May 26, 2022", 13 pgs.

"U.S. Appl. No. 16/821,332, Notice of Allowance mailed Nov. 9, 2022", 9 pgs.

"U.S. Appl. No. 16/821,332, Response filed Aug. 24, 2022 to Non Final Office Action mailed May 26, 2022", 13 pgs.

"European Application Serial No. 20719525.6, Response to Communication pursuant to Rules 161 and 162 filed May 19, 2022", 14 pgs.

"International Application Serial No. PCT/US2020/023112, International Preliminary Report on Patentability mailed Sep. 30, 2021", 8 pgs.

"International Application Serial No. PCT/US2020/023112, International Search Report mailed Jun. 8, 2020", 5 pgs.

"International Application Serial No. PCT/US2020/023112, Written Opinion mailed Jun. 8, 2020", 6 pgs.

Benjamin, Emelia J., et al., "Independent Risk Factors for Atrial Fibrillation in a Population-Based Cohort, The Framingham Heart Study", JAMA, The Journal of the American Medical Association, Mar. 16, 1994, vol. 271, No. 11, 840-844.

Kotecha, Dipak, et al., "Atrial fibrillation in heart failure: what should we do?", European Heart Journal (2015) 36, 3250-3257.

Kotecha, Dipak, et al., "Heart Failure With Preserved Ejection Fraction and Atrial Fibrillation", J Am Coll Cardiol. 2016;68(20):2217-28.

Shah, Sanjiv J., et al., "Association of the Fourth Heart Sound with Increased Left Ventricular End-Diastolic Stiffness", J Card Fail. Jun. 2008 ; 14(5): 431-436.

Verma, Atul, et al., "Treatment of Patients With Atrial Fibrillation and Heart Failure With Reduced Ejection Fraction", Circulation. Apr. 18, 2017;135:1547-1563. DOI: 10.1161/CIRCULATIONAHA.116.026054.

"Chinese Application Serial No. 202080036923.6, Response filed Apr. 15, 2024 to Office Action mailed Jan. 31, 2024", w/ current English claims, 15 pgs.

"European Application Serial No. 20719525.6, Communication Pursuant to Article 94(3) EPC mailed Jul. 11, 2023", 5 pgs.

"European Application Serial No. 20719525.6, Response Filed Oct. 23, 2023 to Communication Pursuant to Article 94(3) EPC mailed Jul. 11, 2023", 11 pgs.

* cited by examiner

SYSTEMS AND METHODS FOR PREDICTING ATRIAL ARRHYTHMIA

CLAIM OF PRIORITY

This application is a continuation of U.S. patent application Ser. No. 16/821,332, filed on Mar. 17, 2020, which claims the benefit of priority under 35 U.S.C. § 119(e) of U.S. Provisional Patent Application Ser. No. 62/820,132, filed on Mar. 18, 2019, which are herein incorporated by reference in their entireties.

TECHNICAL FIELD

This document relates generally to medical devices, and more particularly, to systems, devices and methods for predicting atrial tachyarrhythmia in a subject.

BACKGROUND

Cardiac arrhythmia is an abnormality in the timing or pattern of the heartbeat. Atrial tachyarrhythmia is a cardiac arrhythmia characterized by abnormally fast atrial rate, and can include various types of arrhythmia including atrial fibrillation (AF), atrial flutter (AFL), atrial tachycardia, supraventricular tachycardia, among others. AF is the most common clinical arrhythmia, and accounts for approximately one third of admissions resulting from cardiac rhythm disturbances. During AF, the normal regular sinus rhythm is overwhelmed by disorganized electrical pulses originated from regions in or near an atrium. This can lead to irregular conductions to ventricles, causing inappropriately fast and irregular heart rate. One type of AF is paroxysmal AF, which may last from minutes to days before it stops by itself. Another type known as persistent AF may last for over a week and typically requires medication or other treatment to revert to normal sinus rhythm. The third type, permanent AF, is a condition where a normal heart rhythm cannot be restored with treatment. Persistent AF can become more frequent and result in permanent AF.

Congestive heart failure (CHF or HF) is another major cardiovascular epidemic and affects many people in the United States alone. CHF is the loss of pumping power of the heart, resulting in the inability to deliver enough blood to meet the demands of peripheral tissues. CHF patients typically have enlarged heart with weakened cardiac muscles, resulting in reduced contractility and poor cardiac output of blood. CHF can affect the left heart, right heart or both sides of the heart, resulting in non-simultaneous contractions of the left ventricle and contractions of the right ventricle. Such non-simultaneous contractions, also known as dyssynchrony between the left and right ventricles, can further decrease the pumping efficiency of the heart.

There is a close pathophysiological relationship between AF and CHF. A large percentage of CHF patients may experience AF or other types of atrial tachyarrhythmia. AF may facilitate the development or progression of CHF. CHF may increase the risk for the development of AF. The prevalence of AF in patients with CHF increased in parallel with the severity of CHF.

Ambulatory medical devices (AMDs) have been used for monitoring HF patient. Examples of such ambulatory medical devices can include implantable medical devices (IMDs), subcutaneous medical devices, wearable medical devices or other external medical devices. Some AMDs can include a physiologic sensor that provides diagnostic features.

OVERVIEW

This document discusses, among other things, systems, devices, and methods for identifying patients at an elevated risk of atrial tachyarrhythmia (e.g., AF), and predicting future atrial tachyarrhythmia. An exemplary medical-device system includes an arrhythmia detector circuit configured to receive physiologic information in a patient, generate a signal metric using the received physiologic information, and in an absence of atrial tachyarrhythmia in the patient, generate an indication of arrhythmia risk indicating a patient risk of developing future atrial tachyarrhythmia using the generated signal metric. In accordance with the arrhythmia risk indication, the system can generate an alert, or initiate more aggressive monitoring if a patient identified as having a high risk of atrial tachyarrhythmia.

Example 1 is a medical-device system for assessing a cardiac arrhythmia risk of a patient. The system comprises an arrhythmia predictor circuit configured to: receive physiologic information sensed from the patient; and determine a risk of the patient developing atrial tachyarrhythmia using the received physiologic information.

In Example 2, the subject matter of Example 1 optionally includes the arrhythmia predictor circuit that can be configured to generate a trend of the signal metric, and to predict future atrial tachyarrhythmia using the trend when the patient is free of present atrial tachyarrhythmia.

In Example 3, the subject matter of any one or more of Examples 1-2 optionally includes the arrhythmia predictor circuit that can be configured to generate the indication of arrhythmia risk if a signal metric of the received physiologic information exceeds a threshold or falls within a value range.

In Example 4, the subject matter of any one or more of Examples 1-3 optionally includes the received physiologic information that can include cardiac acceleration information.

In Example 5, the subject matter of Example 4 optionally includes the cardiac acceleration information that can include heart sounds (HS) information, and the arrhythmia predictor circuit can be configured to generate a signal metric using the received physiologic information including a HS intensity or a cardiac timing parameter.

In Example 6, the subject matter of Example 5 optionally includes the generated signal metric that can include one or more of: a first (S1) heart sound intensity; a third (S3) heart sound intensity; or a normalized S3 intensity with respect to S1 intensity.

In Example 7, the subject matter of any one or more of Examples 1-6 optionally includes the received physiologic information that can include thoracic impedance information.

In Example 8, the subject matter of any one or more of Examples 1-7 optionally includes the received physiologic information that can include respiration information.

In Example 9, the subject matter of Example 8 optionally includes the arrhythmia predictor circuit that can be configured to generate one or more signal metrics including one or more of: a respiratory rate; a respiratory volume metric; or a rapid shallow breathing index.

In Example 10, the subject matter of any one or more of Examples 1-9 optionally includes the arrhythmia predictor circuit that can be configured to generate two or more signal metrics using the received physiologic information, and to generate the indication of arrhythmia risk using a combination of the generated two or more signal metrics.

In Example 11, the subject matter of any one or more of Examples 1-10 optionally includes the arrhythmia predictor circuit that can be configured to generate the arrhythmia risk indication using a machine-learning model.

In Example 12, the subject matter of any one or more of Examples 1-11 optionally includes an output circuit that can be configured to present the arrhythmia risk indication to a user, or to generate an alert according to the arrhythmia risk indication.

In Example 13, the subject matter of any one or more of Examples 1-12 optionally includes a therapy circuit that can be configured to generate or adjust a therapy according to the arrhythmia risk indication.

In Example 14, the subject matter of any one or more of Examples 1-13 optionally includes the arrhythmia predictor circuit that can be configured to generate the indication of arrhythmia risk in the absence of atrial tachyarrhythmia further using patient demographic information or patient medical history information.

In Example 15, the subject matter of any one or more of Examples 1-14 optionally includes the arrhythmia predictor circuit that can be configured to, in response to the generated arrhythmia risk indication satisfying a condition, update the received physiologic information or tune an arrhythmia risk stratification parameter.

Example 16 is a method of assessing a cardiac arrhythmia risk of a patient. The method comprises steps of, via an arrhythmia predictor circuit of a medical-device system: receiving physiologic information sensed from the patient; and determining a risk of the patient developing atrial tachyarrhythmia using the received physiologic information.

In Example 17, the subject matter of Example 16 optionally includes generating a trend of the physiologic information, and predicting future atrial tachyarrhythmia using the trend.

In Example 18, the subject matter of any one or more of Examples 16-17 optionally includes generating the indication of arrhythmia risk that can include comparing a signal metric of the received physiologic information to a reference value, and wherein the received physiologic information includes one or more of: cardiac acceleration information; thoracic impedance information; or respiration information.

In Example 19, the subject matter of any one or more of Examples 16-18 optionally includes generating the indication of arrhythmia risk using a machine-learning model.

In Example 20, the subject matter of any one or more of Examples 16-19 optionally includes generating the indication of arrhythmia risk, in the absence of atrial tachyarrhythmia, using patient demographic information or patient medical history information.

In Example 21, the subject matter of any one or more of Examples 16-20 optionally includes presenting the arrhythmia risk indication to a user, or generating an alert according to the arrhythmia risk indication.

In Example 22, the subject matter of any one or more of Examples 16-21 optionally includes updating the received physiologic information or tuning an arrhythmia risk stratification parameter when the generated arrhythmia risk indication satisfies a condition.

In Example 23, the subject matter of Example 1 optionally includes the physiologic information that does not include electrocardiograph or electrogram information.

In Example 24, the subject matter of Example 1 optionally includes the determining the risk of the patient developing atrial tachyarrhythmia that does not include using a history of atrial tachyarrhythmias in that patient.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
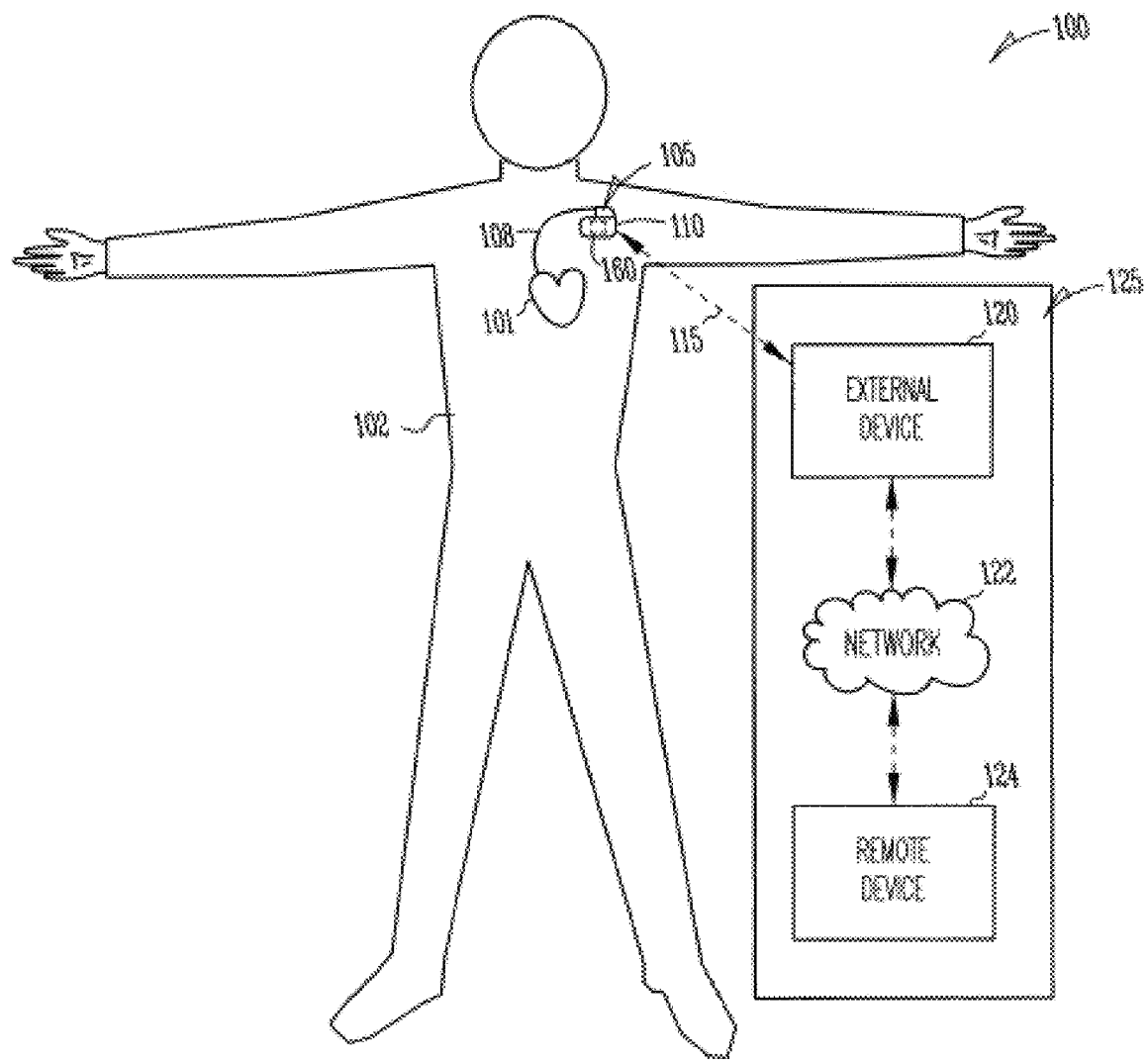
FIG. 1 illustrates generally an example of a patient management system and portions of an environment in which the system may operate.

Atrial tachyarrhythmia, such as AF, can coexist with HF in many CHF patients. Clinical trials have reported an AF prevalence of approximately 20-40% in CHF patients. Presence of CHF has been shown to be an independent risk factor predisposing patients to AF. This may be partly due to the cardiac structural changes (e.g., enlargement, fibrosis) and systemic changes (e.g., neurohormonal imbalance) attributed to CHF, which may create profibrillatory conditions that assist AF development. On the other hand, presence of AF may facilitate worsening of heart failure (WIIF). For example, during AF, irregularity of the ventricular contractions may cause a reduction in left ventricular (LV) filling during short cycles, which may not be completely compensated for by increased filling during longer cycles. The loss of effective atrial contractile function may contributes to the deterioration of LV filling, particularly in CHF patients with diastolic dysfunction. Presence of untreated or uncontrolled AF may also reduce effectiveness of CHF therapies.

Timely and reliable detection of atrial tachyarrhythmia such as AFE is necessary for treating or controlling AF, as well as for preventing or reducing its exacerbating effect on CHF. Conventional AF detection is typically based on patient electrocardiograph (ECG) or symptoms. Patient with AF may frequently experience inappropriately rapid heart rate and irregular ventricular rhythm. As such, AF may be detected based on fast atrial rate and/or irregular ventricular contractions presented in electrophysiological recordings, such as ECG or intracardiac or subcutaneous electrogram (EGM) acquired by an ambulatory monitor. However, the electrophysiological documentation may be susceptible to noise or interferences of physiological or non-physiological sources, and irregular ventricular contractions may be caused by confounding factors other than AF, such as ventricular ectopic contracts or improper sensing of ventricular contractions. As a result, ECG-based methods may result in false positive or false negative AF detections. Additionally, ECG or EGM documentation may not be readily available for patients without ambulatory ECG monitors or implantable cardiac devices.

Atrial tachyarrhythmia such as AF can be asymptomatic in some patients. Asymptomatic AF is prevalent in CHF patients, who are at risk of complications associated with undiagnosed atrial arrhythmias. In contrast to those CHF patients with baseline AF (e.g., permanent or persistent AF co-existing with HF), some CHF patients have no AF history at the time of their HF diagnosis, but may develop new-onset AF events months or years after the diagnosis and management of their CHF conditions. Patients who are in HF conditions for a longer time may have a higher incidence of developing new-onset AF as their HF conditions progress. The new-onset AF, either symptomatic or asymptomatic, may prognosticate worse outcomes in CHF patients. Some clinical studies have shown that new-onset AF may pose a higher risk of mortality and HF hospitalization than CHF patients with baseline AF. At least due to the vicious cycle between AF and HF and particularly the high prevalence of new-onset AF and asymptomatic AF in CHF population, the present inventors have recognized there remains a considerable need of improved systems and methods to proactively identify patients at high risk of atrial tachyarrhythmia like AF, predict future AF events before an occurrence of clinical manifestations, such as electrophysiological presentation or patient being symptomatic. With the risk stratification and atrial tachyarrhythmia prediction discussed herein, the identified high-risk patients may be more aggressively monitored, or appropriate preventive intervention may be implemented.

Disclosed herein are systems, devices, and methods for assessing a cardiac arrhythmia risk of a patient, such as a risk for developing atrial fibrillation. An exemplary medical-device system includes an arrhythmia predictor circuit configured to receive physiologic information of the patient, and generate a signal metric using the received physiologic information. In an absence of atrial tachyarrhythmia, the arrhythmia predictor circuit may generate an indication of arrhythmia risk of the patient developing future atrial tachyarrhythmia using the generated signal metric. In accordance with the arrhythmia risk indication, the system may generate an alert, or initiate more aggressive monitoring in patients identified with a high atrial tachyarrhythmia risk.

Various embodiments discussed in this document may help improve the medical technology of automated, device-based patient AF risk stratification and prediction of future AF events. The AF risk stratification and prediction as disclosed herein may help prevent progressing into persistent or permanent AF, and reduce the chance or slow down the worsening of heart failure (WHF). Conventional AF detection techniques, such as those based on ECG/EGM or patient symptoms, do not adequately address new-onset AF or asymptomatic AF events, such as in CHF patients with no history of atrial tachyarrhythmia. Electrophysiological characteristics such as fast atrial rate or irregular ventricular contractions may indicate an onset of a current (e.g., ongoing) AF event, but may not reliably identify patient AF risk or predict future AF, when the patient is free of AF or other atrial tachyarrhythmia at present, or in patients having no history of AF or other atrial tachyarrhmia. In contrast, according to some embodiments, the systems and methods discussed herein uses a multi-sensor approach to proactively identify patients at high risk of AF days or several months before an AF event develops and clinically diagnosed based on electrophysiological manifestation or patient symptoms. The early indications disclosed herein, such as represented by changes in one or more sensor responses, may enable automatic AF risk stratification and prediction of future AF events. Alerts may be generated and provided to clinicians or other healthcare personnel, such that the identified high-risk patients may be more aggressively monitored, or preventive intervention may be implemented. As a result, patient outcome may be improved, and healthcare cost associated with AF and WHF management may be reduced. Moreover, the improvement in AF management as discussed herein can be achieved with little to no additional cost or added system complexity. In some examples, existing system performance (e.g., HF diagnostics and therapy, and AF or other arrhythmia detection and treatment, etc.) can be maintained using lower cost or less obtrusive systems, apparatus, and methods. With improved risk stratification and AF event prediction, subsequent resources for WHF and AF management can be reduced, ambulatory device's battery life can be extended, fewer unnecessary drugs and procedures may be scheduled, prescribed, or provided, and overall system cost and power savings may be realized in contrast to existing devices and systems.

FIG. 1 illustrates generally an example of a patient management system 100 and portions of an environment in which the system 100 may operate. The patient management system 100 may perform a range of activities, including remote patient monitoring and diagnosis of a disease condition. Such activities can be performed proximal to a patient, such as in the patient's home or office, through a centralized server, such as in a hospital, clinic or physician's office, or through a remote workstation, such as a secure wireless mobile computing device.

The patient management system 100 may include an ambulatory system 105 associated with a patient 102, an external system 125, and a telemetry link 115 providing for communication between the ambulatory system 105 and the external system 125.

The ambulatory system 105 may include an ambulatory medical device (AMD) 110. In an example, the AMD 110 may be an implantable device subcutaneously implanted in a chest, abdomen, or other parts of the patient 102. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The AMD 110 alternatively or additionally may include a subcutaneous medical device such as a subcutaneous monitor or diagnostic device, external monitoring or therapeutic medical devices such as automatic external defibrillators (AEDs) or Holter monitors, or wearable medical devices such as patch-based devices, smart watches, or smart accessories.

By way of example, the AMD 110 may be coupled to a lead system 108. The lead system 108 may include one or more transvenously, subcutaneously, or non-invasively placed leads or catheters. Each lead or catheter may include one or more electrodes. The arrangements and uses of the lead system 108 and the associated electrodes may be determined using the patient need and the capability of the AMD 110. The associated electrodes on the lead system 108 may be positioned at the patient's thorax or abdomen to sense a physiologic signal indicative of cardiac activity, or physiologic responses to diagnostic or therapeutic stimulations to a target tissue. By way of example and not limitation, and as illustrated in FIG. 1, the lead system 108 may be surgically inserted into, or positioned on the surface of, a heart 101. The electrodes on the lead system 108 may be positioned on a portion of a heart 101, such as a right atrium (RA), a right ventricle (RV), a left atrium (LA), or a left ventricle (LV), or any tissue between or near the heart portions. In some examples, the lead system 108 and the associated electrodes may alternatively be positioned on other parts of the body to sense a physiologic signal containing information about patient heart rate or pulse rate. In an example, the ambulatory system 105 may include one or more leadless sensors not being tethered to the AMD 110 via the lead system 108. The leadless ambulatory sensors may be configured to sense a physiologic signal and wirelessly communicate with the AMD 110.

The AMD 110 may be configured as a monitoring and diagnostic device. The AMD 110 may include a hermetically sealed can that houses one or more of a sensing circuit, a control circuit, a communication circuit, and a battery, among other components. The sensing circuit may sense a physiologic signal, such as using a physiologic sensor or the electrodes associated with the lead system 108. Examples of the physiologic signal may include one or more of electrocardiogram, intracardiac electrogram, arrhythmia, heart rate, heart rate variability, intrathoracic impedance, intracardiac impedance, arterial pressure, pulmonary artery pressure, left atrial pressure, right ventricular (RV) pressure, left ventricular (LV) coronary pressure, coronary blood temperature, blood oxygen saturation, one or more heart sounds, intracardiac acceleration, physical activity or exertion level, physiologic response to activity, posture, respiration rate, tidal volume, respiratory sounds, body weight, or body temperature.

The AMD 110 may include a physiologic event detector circuit 160 configured to detect a physiologic event of a patient. In an example, the physiologic event detector circuit 160 may be configured to assess a cardiac arrhythmia risk in a patient, and predict a future cardiac arrhythmic event using the sensed physiologic signals. Examples of the cardiac arrhythmia may include AF, AFL, atrial tachycardia, supraventricular tachycardia, ventricular tachycardia, or ventricular fibrillation, cardiac pauses, among other brady- or tachy-arrhythmia. In some examples, the physiologic event detector circuit 160 may be configured to detect worsening of a chronic medical condition, such as worsening of heart failure (WHF). The physiologic event detector circuit 160 may execute a detection algorithm to monitor one or more physiologic signals continuously or periodically, and to detect the physiologic event automatically. Additionally or alternatively, the physiologic event detector circuit 160 may be configured to operate in a patient-triggered mode, register a patient-triggered episode and record physiologic data in response to a user-activated trigger. The trigger may be activated by the patient when the patient demonstrates certain signs or symptoms, or experiences a precursor event indicative of a medical event.

The AMD 110 may alternatively be configured as a therapeutic device configured to treat arrhythmia or other heart conditions. The AMD 110 may additionally include a therapy unit that may generate and deliver one or more therapies. The therapy may be delivered to the patient 102 via the lead system 108 and the associated electrodes. The therapies may include electrical, magnetic, or other types of therapy. The therapy may include anti-arrhythmic therapy to treat an arrhythmia or to treat or control one or more complications from arrhythmia, such as syncope, congestive heart failure, or stroke, among others. Examples of the anti-arrhythmic therapy may include pacing, cardioversion, defibrillation, neuromodulation, drug therapies, or biological therapies, among other types of therapies. In an example, the therapies may include cardiac resynchronization therapy (CRT) for rectifying dyssynchrony and improving cardiac function in CHF patients. In some examples, the AMD 110 may include a drug delivery system such as a drug infusion pump to deliver drugs to the patient for managing arrhythmia or complications from arrhythmia.

The external system 125 may include a dedicated hardware/software system such as a programmer, a remote server-based patient management system, or alternatively a system defined predominantly by software running on a standard personal computer or a mobile device. The external system 125 may manage the patient 102 through the AMD 110 connected to the external system 125 via a communication link 115. This may include, for example, programming the AMD 110 to perform one or more of acquiring physiologic data, performing at least one self-diagnostic test (such as for a device operational status), analyzing the physiologic data to detect a cardiac arrhythmia, or optionally delivering or adjusting a therapy to the patient 102. Additionally, the external system 125 may receive device data from the AMD 110 via the communication link 115. Examples of the device data received by the external system 125 may include real-time or stored physiologic data from the patient 102, diagnostic data such as detection of cardiac arrhythmia or events of worsening heart failure, responses to therapies delivered to the patient 102, or device operational status of the AMD 110 (e.g., battery status and lead impedance). The telemetry link 115 may be an inductive telemetry link, a capacitive telemetry link, or a radio-frequency (RF) telemetry link, or wireless telemetry based on, for example, "strong" Bluetooth or IEEE 802.11 wireless fidelity "WiFi" interfacing standards. Other configurations and combinations of patient data source interfacing are possible.

By way of example and not limitation, the external system 125 may include an external device 120 in proximity of the AMD 110, and a remote device 124 in a location relatively distant from the AMD 110 in communication with the external device 120 via a telecommunication network 122. Examples of the external device 120 may include a programmer device.

The remote device 124 may be configured to evaluate collected patient data and provide alert notifications, among other possible functions. In an example, the remote device 124 may include a centralized server acting as a central hub for collected patient data storage and analysis. The server may be configured as a uni-, multi- or distributed computing and processing system. The remote device 124 may receive patient data from multiple patients including, for example, the patient 102. The patient data, such as medical event episodes, may be collected by the AMD 110, among other data acquisition sensors or devices associated with the patient 102. The remote device 124 may include a storage unit to store the patient data in a patient database. The storage unit may additionally store an association between a plurality of episode characterizations and a plurality of detection algorithms for detecting a medical event having respective episode characterizations. The server may process the device-generated event episodes to verify that a specific medical event (e.g., a cardiac arrhythmia type) is detected such that the device-detected event is a true positive (TP) detection; or that no such medical event is detected such that the device-detected event is a false positive (FP) detection. The processing of the device-generated medical event episodes may be based on a stored association. In an example, a first event episode may be presented to a user (e.g., a clinician), who would provide an adjudication decision and a first episode characterization. If the adjudication decision indicates that the first event episode is a FP detection, then the server may identify from the stored association a detection algorithm corresponding to the first episode characterization, and process a second event episode using at least the identified detection algorithm to determine that the second event episode is either a TP or a FP detection. The server may schedule a presentation of at least a portion of the second episode using the processing result of the second episode. By using the detection algorithms tailored for recognizing episode with an episode characterization associated with a FP episode, more FP episodes having the same or similar episode characterization may be identified, and therefore avoided from being reviewed and adjudicated by the user. If the second event episode is determined to be a TP episode, then an alert is generated indicating further user review may be warranted.

By way of example, alert notifications may include a Web page update, phone or pager call, E-mail, SMS, text or "Instant" message, as well as a message to the patient and a simultaneous direct notification to emergency services and to the clinician. Other alert notifications are possible. In some examples, the server may include a medical event prioritizer circuit configured to prioritize the alert notifications. For example, an alert of a detected medical event may be prioritized using a similarity metric between the physiologic data associated with the detected medical event to physiologic data associated with the historical alerts.

The remote device 124 may additionally include one or more locally configured clients or remote clients securely connected over the network 122 to the server. Examples of the clients may include personal desktops, notebook computers, mobile devices, or other computing devices. Users, such as clinicians or other qualified medical specialists, may use the clients to securely access stored patient data assembled in the database in the server, and to select and prioritize patients and alerts for health care provisioning. The remote device 124, including the server and the interconnected clients, may execute a follow-up scheme by sending follow-up requests to the AMD 110, or by sending a message or other communication to the patient 102, clinician or authorized third party as a compliance notification.

The network 122 may provide wired or wireless interconnectivity. In an example, the network 122 may be based on the Transmission Control Protocol/Internet Protocol (TCP/fP) network communication specification, although other types or combinations of networking implementations are possible. Similarly, other network topologies and arrangements are possible.

One or more of the external device 120 or the remote device 124 may output the detected medical events to a user such as the patient or a clinician, or to a process including, for example, an instance of a computer program executable in a microprocessor. In an example, the process may include an automated generation of recommendations for a therapy, or a recommendation for further diagnostic test or treatment. In an example, the external device 120 or the remote device 124 may respectively include display units for displaying the physiologic or functional signals, or alerts, alarms, emergency calls, or other forms of warnings to signal the detection of arrhythmia. In some examples, the external system 125 may include an external data processor configured to analyze the physiologic or functional signals received by the AMD 110, and to confirm or reject the detection of the medical events. Computationally intensive algorithms, such as machine-learning algorithms, may be implemented in the external data processor to process the data retrospectively to detect cardia arrhythmia.

Portions of the AMD 110 or the external system 125 may be implemented using hardware, software, firmware, or combinations thereof. Portions of the AMD 110 or the external system 125 may be implemented using an application-specific circuit that may be constructed or configured to perform one or more particular functions, or may be implemented using a circuit that may be programmed or otherwise configured to perform one or more functions. Such a circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a circuit that may be driven by a code instructing a portion of the circuit to perform a comparison between the two signals.

Figure 2:
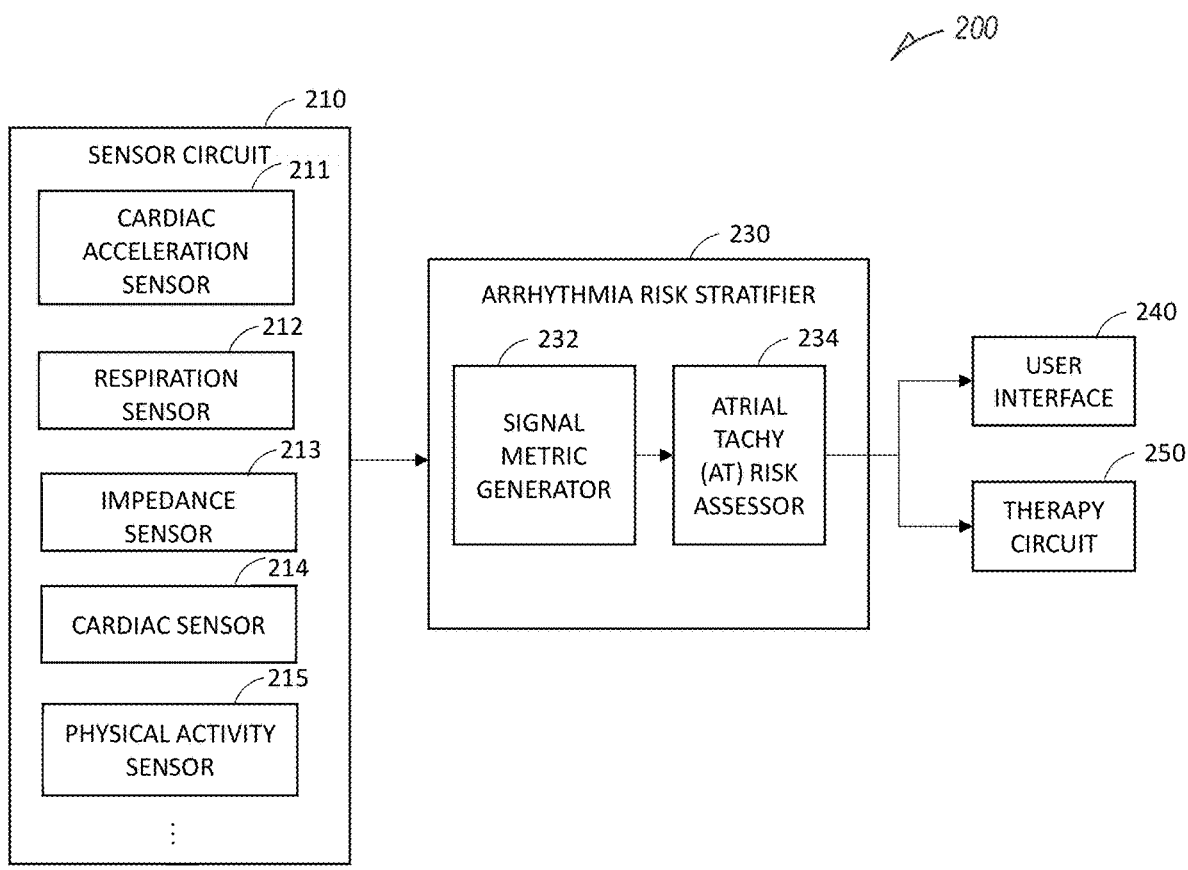
FIG. 2 illustrates generally an example of an arrhythmic risk stratification system configured to assess a cardiac arrhythmia (e.g., AF) risk in a patient.

FIG. 2 illustrates generally an example of an arrhythmic risk stratification system 200 configured to assess a cardiac arrhythmia (e.g., AF or other atrial tachyarrhythmia) risk in a patient when the patient is presently free of atrial tachyarrhythmia, or in patients having no history of AF or other atrial tachyarrhythmia Portions of the arrhythmic risk stratification system 200 may be included in the physiologic event detector circuit 160 of the AMD 110.

The arrhythmic risk stratification system 200 may include one or more of a sensor circuit 210, an arrhythmia risk stratifier 230, and a user interface unit 240. In some examples, the arrhythmic risk stratification system 200 may additionally include an optional therapy circuit 250. The sensor circuit 210 may include one or more data acquisition circuits and amplifier circuits to sense one or more physiologic signals from a patient via one or more implantable, wearable, or otherwise ambulatory sensors or electrodes associated with the patient. The sensor circuit 210 may include one or more other sub-circuits to digitize, filter, or perform other signal conditioning operations on the sensed physiologic signal. In some examples, the physiologic signals may be stored in a storage device such as an electronic medical record system. The sensor circuit 210 may retrieve a physiologic signal from the storage device in response to a command signal that is provided by a system user, or automatically generated in response to occurrence of a specific event.

By way of example and not limitation, the sensor circuit 210 may include one or more of a cardiac acceleration sensor 211, a respiration sensor 212, an impedance sensor 213, a cardiac sensor 214, or a physical activity sensor 215.

The cardiac acceleration sensor 211 may include an accelerometer or a microphone sensor, and be configured to sense or otherwise receive cardiac vibrational or acoustic information. In an example, the cardiac acceleration information incudes heart sounds information. Heart sounds are associated with mechanical vibrations from activity of a patient's heart and the flow of blood through the heart. Heart sounds recur with each cardiac cycle and are separated and classified according to the activity associated with the vibration. The HS information may include, but not limited to, intensity (e.g., amplitudes or signal power) of one or more of first (S1), second (S2), third (S3), or fourth (S4) heart sounds components. S1 is associated with the vibrational sound made by the heart during tensing of the mitral valve. S2 marks the beginning of diastole. S3 can be related to filling pressures of the left ventricle during diastole. S4 is associated with atrial contraction. Additionally or alternatively, the HS information may include cardiac timing parameters, such as systolic time intervals measured using one or more said HS components.

The respiration sensor 212 may be configured to sense a respiration signal from the patient. In an example, the respiration sensor 212 may be coupled to electrodes attached to or implanted in the patient to sense a respiration signal. The respiration signal includes a respiration waveform that represents the change of airflow or lung volume during a respiratory cycle. The respiration sensor may include a flowmeter configured to sense directly the airflow in the respiratory system or volume change in the lungs. Alternatively, the respiration sensor may sense a physiological signal modulated by respiration, such as a thoracic impedance signal measured using electrodes on or inside patient chest (e.g., electrodes associated with an implantable lead). In some examples, a respiration sensor may sense other respiration-modulated physiological signals, such as a chest muscle strain sensor configured to measure cyclic changes in muscle tension corresponding to respiration cycles, an accelerometer configured to measure acceleration associated with displacement or movement of chest walls corresponding to respiration, or an acoustic or vibrational signal modulated by respiration. Other examples of the respiration sensor may include a patient-external respiratory band, a respiration flowmeter, and an implantable or patient-external breath sound detector, among other sensors configured to sense a respiration-modulated physiological signal.

The impedance sensor 213 may be configured to sense impedance, such as thoracic impedance, in the patient. The thoracic impedance may be measured using electrodes associated with an implantable lead. In an example, the thoracic impedance may be sensed between an electrode on a right ventricular and the can housing of and implantable device implanted at the left or right pectoral region. In another example, the thoracic impedance may be sensed between an electrode on a left ventricle and the can housing of the implantable device, or between a right atrium electrode and the can housing of the implantable device. The thoracic impedance may alternatively be measured using non-invasive surface electrodes removably attached to a patient chest.

The cardiac sensor 214 may be configured to receive cardiac information, such as an electrocardiograph (ECG) such as sensed from electrodes on the body surface, a subcutaneous ECG such as sensed from electrodes placed under the skin, or an intracardiac electrogram (EGM) such as sensed from the one or more electrodes on the lead system 108. Cardiac parameters may be derived using the cardiac electric information, such as heart rate, heart rate variability, cardiac synchrony, conduction abnormalities, among others.

The physical activity sensor 215 can be configured to receive information about a physical motion (e.g., activity, steps) or posture or position information. The physical activity sensor 215 can include an implantable, wearable, holdable, or otherwise ambulatory sensor for sensing physical activity. The physical activity sensor may include a single-axis or a multi-axis accelerometer configured to sense an acceleration signal of at least a portion of the subject's body. The strength of the acceleration signal can be indicative of the physical activity level. The physical activity, motion, or posture or position information may additionally or alternatively be used to trigger one or more other physiologic sensors, such as heart sounds, impedance, or pressure data acquired under a specified physical activity level or a specified posture. Physical activity information, and/or physiologic responses (e.g., sensed by other physiologic sensors) to activity, may be used to assess arrhythmic risk in a HF patient, such as a risk of developing a future AF event.

It is to be understood that the physiologic sensors 211-215 illustrated in FIG. 2 are non-limiting examples of sensors used for arrhythmia risk stratification and AF event prediction, according to various embodiments discussed in this document. By way of non-limiting example, a pressure sensor may be used to receive blood pressure information, such as arterial pressure signal, pulmonary artery pressure signal, left atrial pressure signal, RV pressure signal, LV coronary pressure signal, etc. In another example, a temperature sensor may be configured to receive body temperature information. Examples of the body temperature sensor may be include a thermal couple, a thermistor, an infrared sensor, or a temperature sense integrated circuit. In an example, a blood oxygen sensor (e.g., a pulse oximeter) may be configured to receive information about blood oxygen saturation. In another example, a chemical sensor may be configured to receive information of one or more chemicals in blood fluid (e.g., blood), such as brain natriuretic peptide (BNP), blood panel, sodium and potassium levels, glucose level and other biomarkers and bio-chemical markers, among others. One or more of those additional sensors discussed above may be included in the system 200, in addition to or in lieu of any of the sensors 211-215, and used for arrhythmia risk stratification and AF event prediction. In some examples, the physiologic information received by the sensor circuit 210 may include information from the sensor (s) as discussed above excluding electrocardiograph or electrogram information.

The arrhythmic risk stratifier 230 may assess a cardiac arrhythmia risk in a patient, and in some examples, predict a future cardiac arrhythmic event such as an AF event, using the physiologic information received from the sensor circuit 210. The arrhythmic risk stratifier 230 may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general-purpose processor that may receive and execute a set of instructions of performing the functions, methods, or techniques described herein.

The arrhythmic risk stratifier 230 may include circuit sets comprising one or more other circuits or sub-circuits, including a signal metric generator 232 and an atrial tachyarrhythmia risk assessor 234. These circuits or sub-circuits may, individually or in combination, perform the functions, methods or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The signal metric generator 232 may generate a signal metric using the received physiologic information, such as one or more physiological signals sensed by any of the sensors 211-215. The signal metric may include statistical parameters extracted from the sensed physiological signal, such as signal mean, median, or other central tendency measures or a histogram of the signal intensity, among others. In some examples, the signal metric may include morphological parameters extracted from the sensed physiological signal, such as maximum or minimum within a specified time period such as a cardiac cycle, positive or negative slope or higher order statistics, signal power spectral density at a specified frequency range, among other morphological parameters.

In an example, the signal metrics may include HS metrics. The HS metrics may include intensity of one or more HS components S1, S2, S3, or S4. The intensity may be represented by an amplitude of a HS component in a time-domain HS signal, a transformed HS signal such as integrated HS energy signal, or in a frequency-domain HS signal such as the peak value of the power spectral density, or peak value of a generic measurement within the respective HS detection window, such as peak envelop signal or root-mean-squared value of the portion of the HS signal within the HS detection window. The intensity of a HS component may also include a slope or rate of change of signal amplitude or peak energy. In an example, the HS metric may include an intensity measure of a portion of the HS signal that includes at least a portion of a specified HS component, such as a root-mean-squared value of the HS signal portion between an R wave and a subsequent S1 heart sound, or between an R wave and a subsequent S2 heart sound, within the same cardiac cycle. In some examples, the signal metrics may include a composite HS metric, such as a linear or nonlinear combination of two or more of S1, S2, S3, and S4 intensities. Non-limiting examples of the composite HS metric may include a ratio of S3 intensity to S1 intensity, S3/S1, or a ratio of S4 intensity to S1 intensity, S4/S1.

The HS metrics may additionally or alternatively include HS-based cardiac timing parameters, such as cardiac timing intervals (CTI). The CTI may represent electromechanical coupling of the heart, and be indicative of cardiac functionality and hemodynamic status. Examples of the CTI may include a pre-ejection period (PEP) such as measured between the onset of the QRS to the S1 heart sound, a systolic timing interval (STI) such as measured between the onset of the QRS complex on the ECG to the S2 heart sound, a left-ventricular ejection time (LVET) such as measured as an interval between S1 and S2 heart sounds, or a diastolic timing interval (DTI) such as measured between the S2 heart sound and the onset of the subsequent QRS complex on the ECG, among others. In some examples, the HS metric generator circuit 222 may generate composite measures such as PEP/LVET ratio, STI/DTI ratio, STI/cycle length (CL) ratio, or DTI/CL ratio, among others. The HS intensity or the HS-based cardiac timing parameters may be used to detect, in CHF patients having an atrial tachyarrhythmia risk, reduction in one or more of cardiac contractility, ejection fraction, systolic blood pressure, or cardiac output, or an increase in end-diastolic volume. The present inventors have recognized that some HS metrics may be predictive of a patient risk of developing a future atrial arrhythmic event like AF, as illustrated in FIGS. 5B-5C and to be discussed further below.

In an example, the signal metric generator 232 may generate from the received respiration information one or more respiration metrics. Examples of the respiration metrics may include a tidal volume, a respiration rate, a minute ventilation, a respiratory sound, a rapid-shallow breathing index (RSBI) computed as a ratio of respiratory rate to tidal volume, an apnea hypopnea index, among others. The present inventors have recognized that an individual or a combination of said respiration parameters may be predictive of a patient risk of developing a future atrial arrhythmic event like AF, as illustrated in FIGS. 5D-5E and to be discussed further below.

In another example, the signal metric generator 232 may generate a thoracic impedance magnitude metric using the received impedance information. As illustrated in FIG. 5F and to be discussed further below, the thoracic impedance magnitude may be predictive of a patient risk of developing a future atrial arrhythmic event like AF.

The atrial tachyarrhythmia risk assessor 234 may be configured to generate, in the absence of atrial tachyarrhythmia in the patient, an arrhythmia risk indication indicating a risk of the patient developing future atrial tachyarrhythmia using the signal metric generated by the signal metric generator 232. For example, the atrial tachyarrhythmia risk assessor 234 may determine that a patient has a high atrial tachyarrhythmia risk when the signal metric satisfies a specific criterion, such as exceeding a threshold or falling in a specified value range.

In an example, the atrial tachyarrhythmia risk assessor 234 may generate a trend of the signal metric. The signal metric trend include multiple measurements of the signal metric over a period of time. In an example, the signal metric trend may include a daily trend including daily measurements of a signal metric over a specified number of days. The daily measurements may be performed during a particular time of a day (e.g., nighttime, morning, or afternoon), or during a specified patient state (e.g., when the patient is awake or asleep). The measurements may last for a specified duration (e.g., approximately 2-8 hours). Examples of signal metric trends are discussed below, such as with reference to FIGS. 5B-5F. In an example, the atrial tachyarrhythmia risk assessor 234 may include a comparator to compare the signal metric trend to a threshold, or a reference level of the signal metric, and generate the arrhythmia risk indication based on the comparison. The threshold may include a patient-specific baseline measurement of the signal metric when the patient is free of arrhythmias, or based on population data. In some examples, the comparison may be carried out between a representative signal metric value and the threshold. The representative signal metric value may include a central tendency (e.g., a mean, a median, or a mode) of multiple measurements taken over a time period. For example, an arrhythmia risk indication may indicate a high AF risk if a representative S1 intensity exceeds an S1 threshold by a specified margin, or if a representative S3 intensity exceeds an S3 threshold by a specified margin, or if a representative respiration rate (RR) exceeds an RR threshold by a specified margin, or if a representative RSBI exceeds an RSBI threshold by a specified margin, or if a representative thoracic impedance falls below a thoracic impedance threshold by a specified margin.

In some examples, the atrial tachyarrhythmia risk assessor 234 may generate the arrhythmia risk indication using a machine-learning (ML) model. One or more signal metrics, generated using physiologic information acquired by one sensor or multiple sensors, may be fed into the ML model. The ML model may be trained using sensor data from patient population, and produce an arrhythmia risk indication corresponding to the signal metric measurements as input to the model. Examples of the ML model may include a linear regression model, a decision tree, a Naïve Bayes model, a support vector machine model, a K-nearest neighbor model, a random forest model, a neural network model, a voting model, a fuzzy logic model, among others.

The arrhythmia risk indication may be represented by a categorical value (e.g., "high", "medium", or "low" risk) or a numerical value (e.g., on a scale of 1-5, where "1" indicates the lowest risk and "5" indicates the highest risk), which indicate various degrees of arrhythmic risk. Categorization of various arrhythmic risk degrees may be carried out based on a deviation of the measured value of the signal metric from a threshold (e.g., a reference or baseline value of the signal metric). In an example, the arrhythmic risk degrees may be proportional to said deviation, such that the more the signal metric deviates from the threshold, the higher the arrhythmic risk degree is. The atrial tachyarrhythmia risk assessor 234 may predict an onset timing or timeframe of future atrial tachyarrhythmia based on the deviation of the measured signal metric from the threshold. In an example, a correspondence (e.g., a mapping) between said deviation and projected atrial tachyarrhythmia onset time (e.g., in days, weeks, or months from the time of risk assessment) may be created and updated as needed using patient population data, and stored in a memory. The atrial tachyarrhythmia risk assessor 234 may then map a measured deviation associated with a signal metric to a projected AF onset time or timeframe using the stored correspondence.

In some examples, the signal metric generator 232 may generate two or more signal metrics using the received physiologic information. The atrial tachyarrhythmia risk assessor 234 may compare each the two or more signal metrics to their respective thresholds, and generate the arrhythmia risk indication using a combination of generated two or more signal metrics. The combination may include a linear or nonlinear combination, such as a weighted sum, of two or more signal metrics derived from one or more physiological sensors such as any of sensors 211-215. In another example, the signal metric generator 232 may generate a composite signal metric using a combination of signal metrics. The atrial tachyarrhythmia risk assessor 234 may trend the composite signal metric over time, and generate the arrhythmia risk indication using a comparison of the composite signal metric trend and a threshold.

The user interface unit 240 may include an input device and an output device. In an example, at least a portion of the user interface unit 240 may be implemented in the external system 130. The input device may receive a user's programming input, such as parameters for adjusting detection criterion and parameters for detecting cardiac arrhythmia. The input device may include a keyboard, on-screen keyboard, mouse, trackball, touchpad, touch-screen, or other pointing or navigating devices. The input device may enable a system user to program the parameters used for sensing the physiologic signals, detecting arrhythmia, and generating alerts, among others.

The output device may generate a human-perceptible presentation of arrhythmic risk indication. The output device may include a display for displaying the sensed physiologic information, intermediate measurements or computations such as one or more signal metrics, signal metric trends, and categorization of arrhythmic risks, among others. The output unit may include a printer for printing hard copies of information related to patient arrhythmic risk. The information may be presented in a table, a chart, a diagram, or any other types of textual, tabular, or graphical presentation formats. The presentation of the output information may include audio or other media format to alert the system user of the detected arrhythmic events. In an example, the output device may generate an alert, an alarm, an emergency call, or other forms of warnings to signal the system user about patient arrhythmic risk or the prediction of future atrial tachyarrhythmia. The output device may generate a recommendation, such as more aggressive arrhythmia monitoring, further testing to be performed, adjustment of an existing sensor configuration or arrhythmia risk stratification algorithm, scheduling or modifying a patient follow-up schedule, or initiating or adjusting patient medication or other types of treatment.

The optional therapy circuit 250 may be configured to deliver a therapy to the patient in response to the arrhythmic risk indication satisfying a condition, such as exceeding a threshold by a specific margin or being categorized as a high risk of future atrial tachyarrhythmia event. Examples of the therapy may include electrostimulation therapy delivered to the heart, a nerve tissue, other target tissues, a cardioversion therapy, a defibrillation therapy, or drug therapy. In some examples, the therapy circuit 250 may modify an existing therapy, such as adjust a stimulation parameter or drug dosage.

Figure 3:
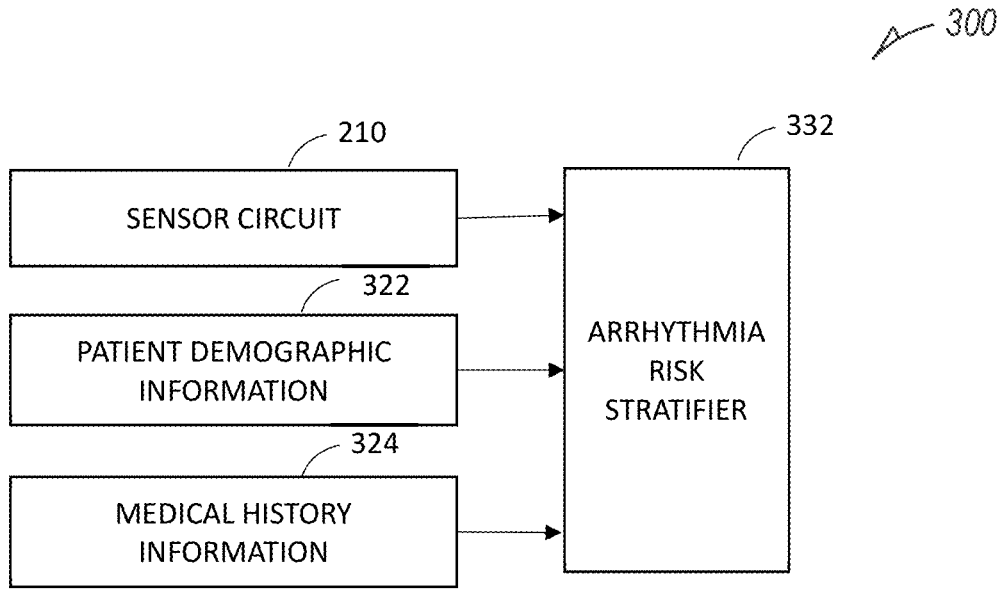
FIG. 3 is a block diagram illustrating an example of portions of an arrhythmia risk stratification system configured to assess a cardiac arrhythmic risk in a patient and to predict future atrial tachyarrhythmia.

FIG. 3 is a block diagram illustrating an example of portions of an arrhythmia risk stratifier medical-device system configured to assess a cardiac arrhythmia (e.g., AF) risk in a patient. The illustrated example can be an example of relevant portions of the arrhythmic risk stratification system 200. For example, the arrhythmia risk stratifier 332 can be an embodiment of the arrhythmia risk stratifier 232, and can be configured to generate an arrhythmic risk indication of the patient developing future atrial tachyarrhythmia in the absence of a present atrial tachyarrhythmia event. Aside from the sensor circuit 210 as shown in the system 200, the arrhythmia risk stratifier 332 may be also coupled to a user input circuit (which can be part of the user interface 240), from which one or both of patient demographic information 322 and patient medical history information 324 may be received. Examples of the patient demographic information 322 may include age, sex, ethnicity, occupation, etc. Examples of the patient medical history information 324 may include indications of patient history of diabetes mellitus, hypertension, myocardial infarction, valvular disease, or one or more HF comorbidities such as obesity, hyperlipidemia, metabolic syndrome, pulmonary dysfunction, sleep-disordered breathing, renal dysfunction, liver dysfunction, anemia, thyroid disorders, skeletal myopathy, depression, and cognitive impairment, among others. In an example, the patient medical history does not include a history of atrial tachyarrhythmias in that patient, such that the arrhythmia risk stratifier 332 determines the risk of the patient developing atrial tachyarrhythmia without using the information of patient atrial tachyarrhythmia history. In an example, the patient medical history information 324 may include time (e.g., years) since patient initial diagnosis of HF. In another example, the patient medical history information 324 may include a composite risk score clinically used to evaluate patient's general risk of arrhythmia, such as a CHADsVASC score that assess a risk of stroke which may influence a decision whether or not to anticoagulate. The CHADsVASC scoring system takes into consideration multiple patient demographics factors and a range of medical history factors, including CHF, hypertension, age, diabetes, stroke/TIA, vascular disease (peripheral arterial disease, previous NI, aortic atheroma).

The arrhythmia risk stratifier 332 may generate the arrhythmic risk indication using the physiologic information from the sensor circuit 210 and one or both of the patient demographic information 322 and the patient medical history information 324. In an example, the atrial tachyarrhythmia risk assessor 234 may generate an arrhythmia risk indication using a combination (e.g., weighted combination) of one or more signal metrics derived from the physiologic information, as well as one or both of the patient demographic information 322 and the patient medical history information 324. In another example, one or more risk stratification parameters used by the arrhythmia risk stratifier 332 (e.g., respective thresholds for various physiologic signal metrics, the threshold for the composite signal metric, or weight factors for respective signal metrics used for generating the arrhythmia risk indication) may be adjusted according to patient demographic information 322 or the patient medical history information 324. For example, if the patient is over 75 years old, or have a CHF, prior stroke, or hypertension, then the thresholds for one or more of HS metrics (e.g., S1 intensity or S3 intensity) or respiration metrics (e.g., RR or RSBI) may be set at a lower level, and/or the threshold for the impedance metric (e.g., thoracic impedance) may be set at a higher level, such that the arrhythmia risk stratifier 332 is more sensitive in predicting an atrial tachyarrhythmia event. In some examples, the ML model implemented in and executed by the arrhythmia risk stratifier 332 may be tuned (e.g., by adjusting a model parameter) according to the patient demographic information 322 or the patient medical history information 324 may be used to tune sensitivity or specificity of the), such that, for example, the ML model can be more sensitive to patients of older age and/or having a history of advanced CHF or other medical conditions.

Figure 4:
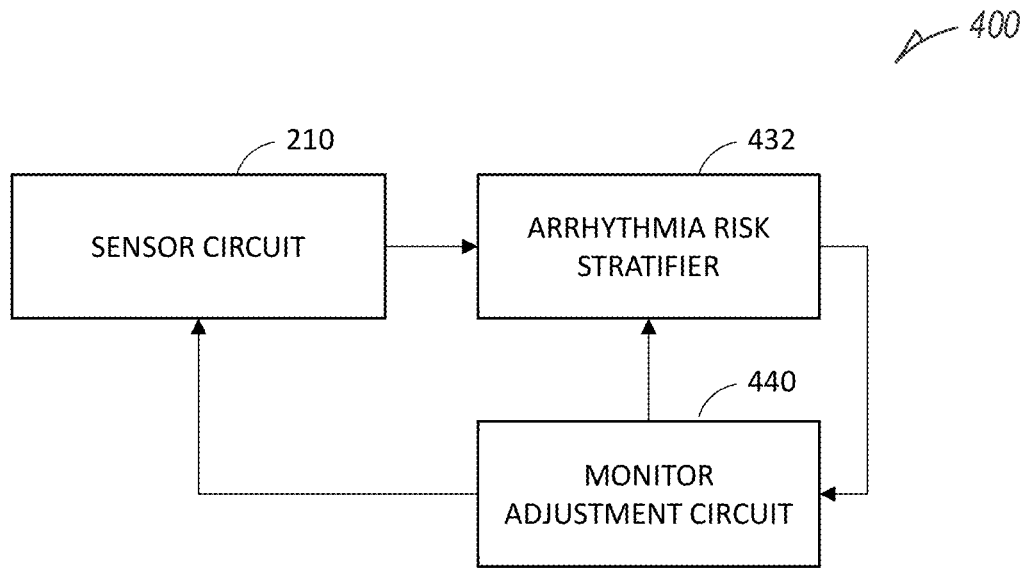
FIG. 4 is a block diagram illustrating an example of portions of an arrhythmia risk stratification system configured to assess a cardiac arrhythmia risk in a patient and adaptively tune the arrhythmia risk assessment based on a current estimate of arrhythmia risk.

FIG. 4 is a block diagram illustrating an example of portions of an arrhythmia risk stratification system configured to assess a cardiac arrhythmia risk in a patient and adaptively tune the arrhythmia risk assessment based on a current estimate of arrhythmia risk. The illustrated system can be an example of relevant portions of the arrhythmic risk stratification system 200. The arrhythmia risk stratifier 432, which is an embodiment of the arrhythmia risk stratifier 232, may be configured to generate an arrhythmic risk indication using physiologic information provided by the sensor circuit 210, as similarly discussed above with reference to FIG. 2. In accordance with the arrhythmic risk indication, a monitor adjustment circuit 440 may be configured to adjust the sensor circuit 210, such as selectively activating or de-activating certain sensors to acquire physiologic information, or adjusting sensor data acquisition time, schedule, frequency, duration, sampling rate, or data precision. For example, if a current arrhythmic risk indication generated by the arrhythmia risk stratifier 432 indicates that the patient has a high AF risk, then the monitor adjustment circuit 440 may tune the sensor circuit 210 to collect more sensor data (e.g., increase data acquisition duration from, e.g., previous 2 hours per day to present 5 hours per day, or increase the data collection frequency from previous once every 3 days to prevent every single day, among other adjustments.

The monitor adjustment circuit 440 may alternatively or additionally tune the arrhythmia risk stratifier 432 according to the arrhythmic risk indication. In an example, the monitor adjustment circuit 440 may modify the signal metrics (e.g., adding a new signal metric, or removing a previously used signal metric) used to generate the arrhythmia risk indication. In another example, the monitor adjustment circuit 440 may tune one or more arrhythmia risk stratification parameters, such as respective thresholds for various physiologic signal metrics, the threshold for the composite signal metric, weight factors for respective signal metrics for generating the arrhythmia risk indication, or a parameter value of a ML model for generating the arrhythmia risk indication. The monitor adjustment circuit 440 may select a different scheme of combing two or more signal metrics, or choose a different ML model, to generate the arrhythmic risk indication. For example, if the current arrhythmic risk indication indicates that the patient has a high AF risk, then more signal metrics may be used, thresholds for individual signal metrics and the threshold for the composite signal metric, or a ML model parameter may be adjusted or a different ML model may be used to improve the sensitivity of predicting an atrial tachyarrhythmia risk. Tuning the arrhythmia risk stratification in adaptation to a present arrhythmic risk indication may enable more aggressive monitoring of high arrhythmia-risk patients in a timely fashion, and improve AF detection as soon as it first occurs. The adaptive tuning of atrial tachyarrhythmia risks stratification may also improve detection of silent AF before causing patient symptoms. In some examples, patients may be timely identified to receive ambulatory monitors (e.g., an implantable cardiac monitor), and appropriate preventive interventions (e.g., oral anticoagulants) may be timely administered.

Figure 5A:
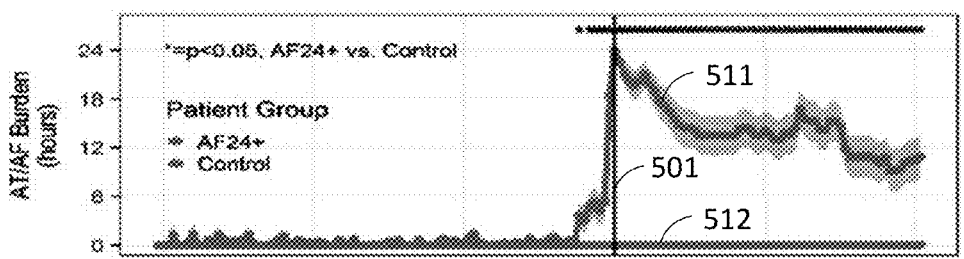
FIGS. 5A-5F are graphs illustrating trends of sensor data recorded from HF patients, which can be used to stratify an atrial tachyarrhythmia risk in a patient.
Figure 5B:
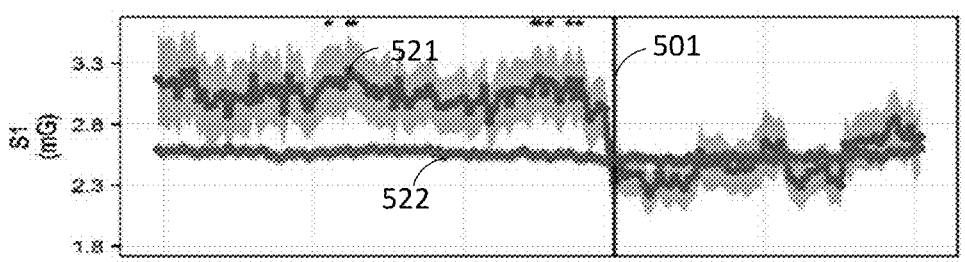
Figure 5C:
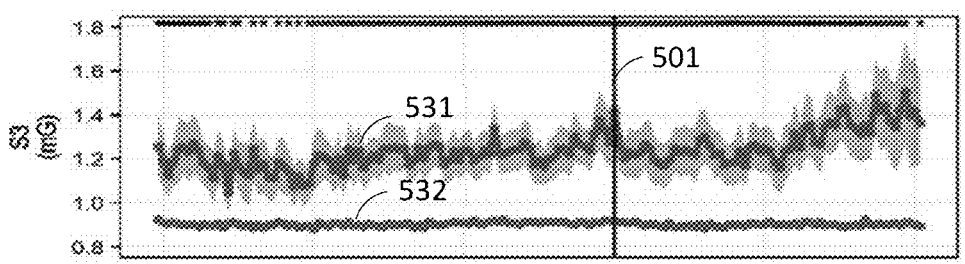
Figure 5D:
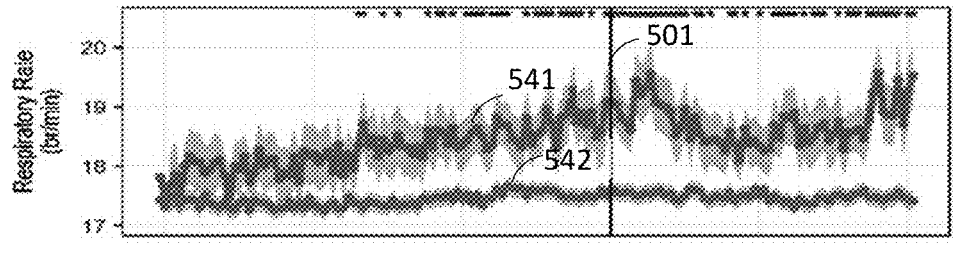
Figure 5E:
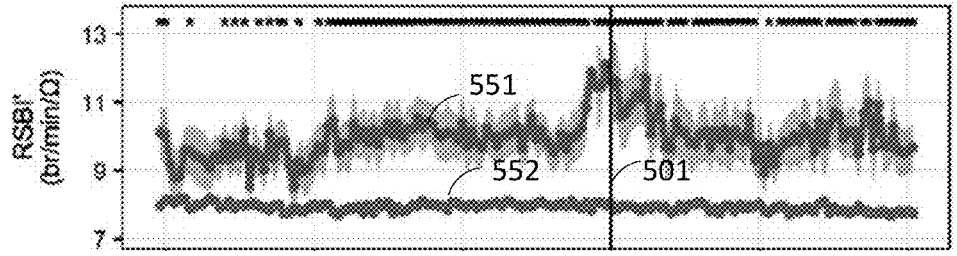
Figure 5F:
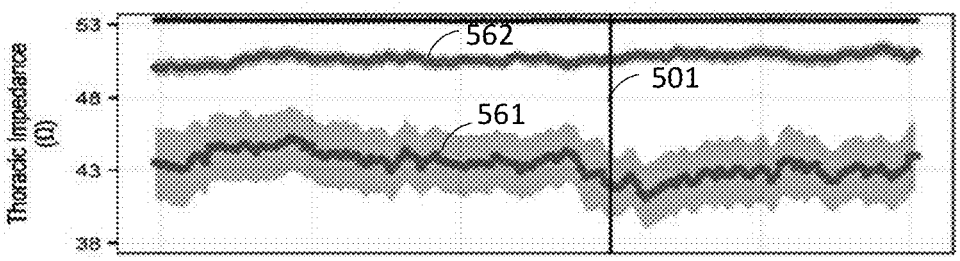

FIGS. 5A-5F are graphs illustrating trends of sensor data recorded from HF patients, which may be used to stratify an atrial tachyarrhythmia (e.g. AF) risk in a patient. The sensor data were recorded before and after a clinically diagnosed AF event occurred in a group of HF patients (hereinafter referred to as "AF group"). The sensor data trends extend from 90 days before, to 60 days after, the diagnosed AF event. The sensor data trends are time-aligned with respect to onset of the diagnosed AF events, corresponding to time '0' (TO) and marked by a vertical solid line 501 in each of graphs 5A-5F. In addition to the sensor data trends of the "AF group", sensor data trends obtained from a "control group" are also shown in graphs 5A-5F for comparison. The control group includes HF patients who did not develop AF during the observation period. Clinical diagnosis of AF, including presence or absence of AF during the observation period (thus classification of a patient into either AF group or control group), onset timing of the AF events, and AF burden (cumulative time spent in AF during a specified unit time like a day), may be adjudicated by a clinician. FIG. 5A illustrates AF burden over time respectively determined for the AF group (trend 511) and the control group (trend 512). As the sensor data trends of the AF group are alighted with respect to AF onset at T0, there are virtually no AF burden before T0. AF burden increases at T0, and stays at a high burden level throughout the 60-day post onset period. No AF burden (at approximately 0) was observed in the control group.

FIGS. 5B-5F illustrate, by way of example and not limitation, trends of various signal metrics using physiologic information such as acquired or received by the sensors 211-215 as illustrated in FIG. 2. In particular, FIG. 5B illustrates an S1 heart sound intensity (e.g., amplitude or signal power) trend (trend 521 for AF group and trend 522 for control group), and FIG. 5C illustrates an S3 heart sound intensity (e.g., amplitude or signal power) trend (trend 531 for AF group and trend 532 for control group). Compared to the control group, the AF group has consistently higher S1 intensity and consistently higher S3 intensity throughout the 90-day period prior to AF onset. The arrhythmia risk stratifier 230 may use S1 intensity or S3 intensity (e.g., by comparing the S1 intensity or S3 intensity to their respective thresholds, or use a ML model as previously discussed) to identify patients with a higher risk of future AF events well before (e.g., 3 months) an AF event is diagnosed.

FIG. 5D illustrates a respiration rate (RR) trend (trend 541 for AF group and trend 542 for control group), and FIG. 5E illustrates a trend of rapid-shallow breathing index (RSBI) defined as the ratio of respiratory frequency to tidal volume (trend 551 for AF group and trend 552 for control group). As shown in FIGS. 5D-5E, both the RR trend and the RSBI trend of the AF group are higher than the respective trends of the control group as far as 90 days prior to AF onset. The distinctly higher RR and higher RSBI become more prominent as time goes and approaches AF onset time T0. Thus, the patients with elevated RR or elevated RSBI may be at a higher risk of developing future AF than those with lower RR or lower RSBI levels, even as far as 90 days prior to AF event actually occurs. The arrhythmia stratifier 230 may compare RR or RSBI to their respective thresholds, and determine an AF risk in the patient, or predict a future AF event, based at least on a deviation of the measured RR or RSBI level to their respective thresholds.

FIG. 5F illustrates a thoracic impedance trend before and after AF onset. The thoracic impedance may be measured using an impedance sensor, which may include electrodes on the skin or subcutaneously placed. The thoracic impedance may be indicative of pulmonary fluid status. As previously discussed, HF patients may have pulmonary fluid buildup or redistribution, thus a low thoracic impedance. FIG. 5F shows that the AF group (trend 561) has consistently a lower thoracic impedance level than the control group (trend 562) throughout the 90-day period prior to AF onset. The arrhythmia stratifier 230 may compare the thoracic impedance to a threshold to identify patients with a higher risk of future AF event, or to predict a future AF event, well before (e.g., 3 months) a clinical diagnosis of an AF event.

Although descriptions above with reference to FIGS. 5B-5F are focused on HS metrics (e.g., S1 and S3), respiration metrics (e.g., RR and RSBI), and impedance metrics (e.g., thoracic impedance magnitude), they are only by way of example and not limitation. Other signal metrics, generated from data of the same or different sensors than discussed above, may be used to stratify AF risk or to predict a future AF event. Also, as previously discussed, two or more signal metrics, either from the same sensor or different sensors, may be combined to generate a composite AF risk indication, using linear or nonlinear combinations, or a machine-learning model.

Figure 6:
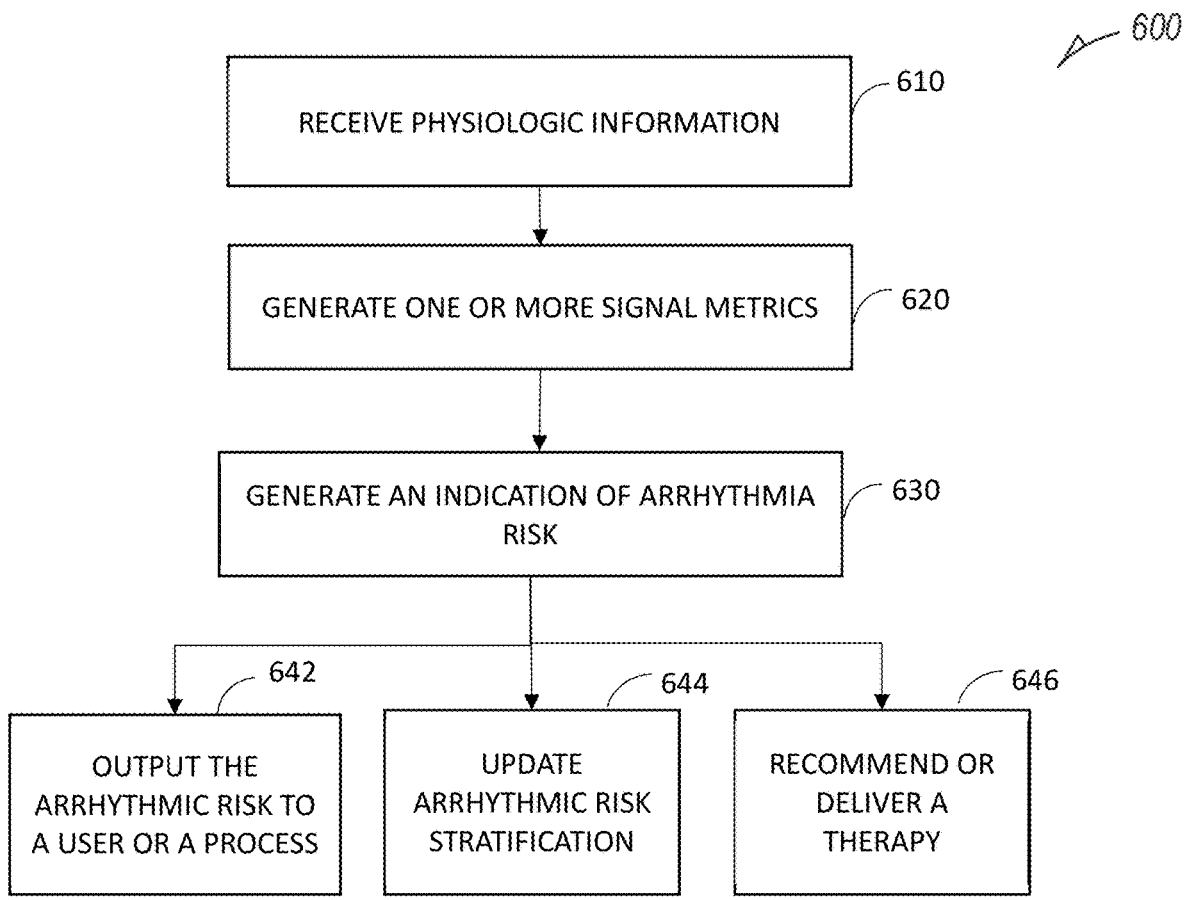
FIG. 6 is a flow chart illustrating an example of a method of assessing a cardiac arrhythmia (e.g., AF) risk in a patient.

FIG. 6 is a flow chart illustrating an example of a method 600 for assessing a cardiac arrhythmia risk in a patient, and predicting a future cardiac arrhythmic event, such as an AF or other atrial tachyarrhythmia events, when the patient is free of atrial tachyarrhythmia. Examples of atrial tachyarrhythmia may include atrial fibrillation (AF), atrial flutter (AFL), and atrial tachycardia, among others. The method 600 may be implemented in and executed by an ambulatory medical device, such as an implantable or wearable medical device, or by a remote patient management system. In an example, the method 600 may be implemented in and executed by the physiologic event detector circuit 160 in the AMID 110, the external system 130, or the arrhythmic risk stratification system 200.

The method 600 commences at 610, where physiologic information of a patient may be received. The physiologic information may be sensed from physiologic sensors associated with a patient, or be retrieved from a storage device (e.g., an electronic medical record system) that stores physiologic signals recorded from a patient. By way of example and not limitation, the physiologic sensors may include any of the sensors 211-215 as illustrated in FIG. 2. Examples of the received physiologic information may include information of cardiac acceleration (e.g., heart sounds), respiration, impedance (e.g., thoracic impedance), cardiac electrical activities, blood pressure, body temperature, blood oxygen, blood chemicals, etc.

At 620, one or more signal metrics may be generated using the received physiologic information, such as using the signal metric generator 232. The signal metrics may include statistical parameters or morphological parameters extracted from the received physiologic information. Examples of the signal metrics may include: heart sounds (HS) metrics such as a HS component intensity (e.g., amplitude or signal power of S1, S2, S3, or S4 heart sounds) or HS-based cardiac timing intervals (CTI); respiration metrics such as tidal volume, a respiration rate, a minute ventilation, a respiratory sound, or a rapid-shallow breathing index (RSBI), or an apnea hypopnea index; thoracic impedance magnitude; pressure metrics such as arterial pressure signal, pulmonary artery pressure signal, left atrial pressure signal, RV pressure signal, LV coronary pressure signal; among others. As illustrated in FIGS. 5A-5F, the present inventors have recognized that at least some of these signal metrics have distinct values (or in distinct value ranges) between an atrial tachyarrhythmia group of HF patients who later developed AF events (e.g., up to 90 days from the date of AF risk assessment), and a control group including HF patients who did not develop AF events, suggesting that the signal metrics can be predictive of a patient risk of developing a future atrial arrhythmic event such as AF.

At 630, an arrhythmia risk indication may be generated in the absence of atrial tachyarrhythmia in the patient, such as using the atrial tachyarrhythmia risk assessor 234. The arrhythmia risk indication indicates a risk of a patient without no atrial tachyarrhythmia history later developing an atrial tachyarrhythmia event (e.g., AF, AFL, or other atrial tachyarrhythmia events). The arrhythmia risk indication may be generated if the signal metric satisfies a specific criterion, such as a value of the signal metric exceeding a threshold or falling in a specified value range. In an example, a signal metric may be trended over time, such as any of the signal metric trends shown in FIGS. 5B-5F. The signal metric trend, or a representative value (e.g., a central tendency of multiple measurements), may be compared to a threshold, or a reference level of the signal metric, to generate the arrhythmia risk indication.

An individual signal metric, or a combination of two or more signal metrics, may be used to generate the arrhythmia risk indication. The combination may include a linear or nonlinear combination, such as a weighted sum. In an example, a composite signal metric may be generated using a combination of signal metrics. The composite signal metric may be trended over time, and compared to a threshold to determine the arrhythmia risk indication. In some examples, various degrees of arrhythmic risk, represented either by categorical or numerical values, may be determined based at least on a deviation of a signal metric, or a composite signal metric, from respective thresholds. In some examples, onset timing, or a timeframe, of future atrial tachyarrhythmia may be predicted based on said deviation. In some examples, the arrhythmia risk indication may be generated using a machine-learning (ML) model, such as a linear regression model, a decision tree, a Naïve Bayes model, a support vector machine model, a K-nearest neighbor model, a random forest model, a neural network model, a voting model, a fuzzy logic model, among others.

The indication of arrhythmia risk generated at 540 may be used in one or more of the processes 642, 644, or 646. At 642, the arrhythmia risk indication may be output to a user or a process, such as via the user interface 240 illustrated in FIG. 2. In an example, the arrhythmia risk indication may be displayed on a display, among other information such as physiologic signals or signal metrics used in the risk assessment process. An alert may be generated according to the arrhythmia risk indication to notify a system user (e.g., a clinician) about patient arrhythmic risk or predicted future atrial tachyarrhythmia events. Alternatively or additionally, at 644, arrhythmia risk stratification may be updated according to the arrhythmic risk indication, such as using the monitor adjustment circuit 440. This may include, for example, selective activating or de-activating certain sensors, adjusting sensor data acquisition time, schedule, frequency, duration, sampling rate, or data precision, modifying the signal metrics (e.g., adding a new signal metric, or removing a previously used signal metric) included in the determination of the arrhythmia risk indication, tuning one or more arrhythmia risk stratification parameters such as respective thresholds for various physiologic signal metrics, the threshold for the composite signal metric, weight factors for respective signal metrics for generating the arrhythmia risk indication, a parameter of the ML model for generating the arrhythmic risk indication, or selecting a different ML model, etc. With the updated arrhythmia risk stratification at 644, more aggressive arrhythmia monitoring may be performed if a high arrhythmia risk is indicated. This accordingly may improve timely detection of AF as soon as it first occurs, as well as improving the identification of silent AF before patients become symptomatic.

Additionally or alternatively, at 646, a recommendation may be generated and provided to the user, such as performing more aggressive arrhythmia monitoring, adjustment of the physiological sensing or arrhythmia risk stratification, initiating or adjusting patient medication. A system user (e.g., a clinician) may review the received physiologic information and the arrhythmic risk indication, and reprogram one or more risk stratification parameters as needed. Additionally or alternatively, at 646, a therapy may be delivered, such as via the optional therapy circuit 250 as illustrated in FIG. 2, in response to the arrhythmic risk indication satisfying a condition, such as exceeding a threshold by a specific margin or being categorized as a high risk of future atrial tachyarrhythmia event. Examples of the therapy may include electrostimulation therapy delivered to the heart, a nerve tissue, other target tissues, a cardioversion therapy, a defibrillation therapy, or drug therapy including delivering drug to a tissue or organ. In some examples, an existing therapy or treatment plan may be modified, such as modifying a patient follow-up schedule or adjusting a stimulation parameter or drug dosage.

Figure 7:
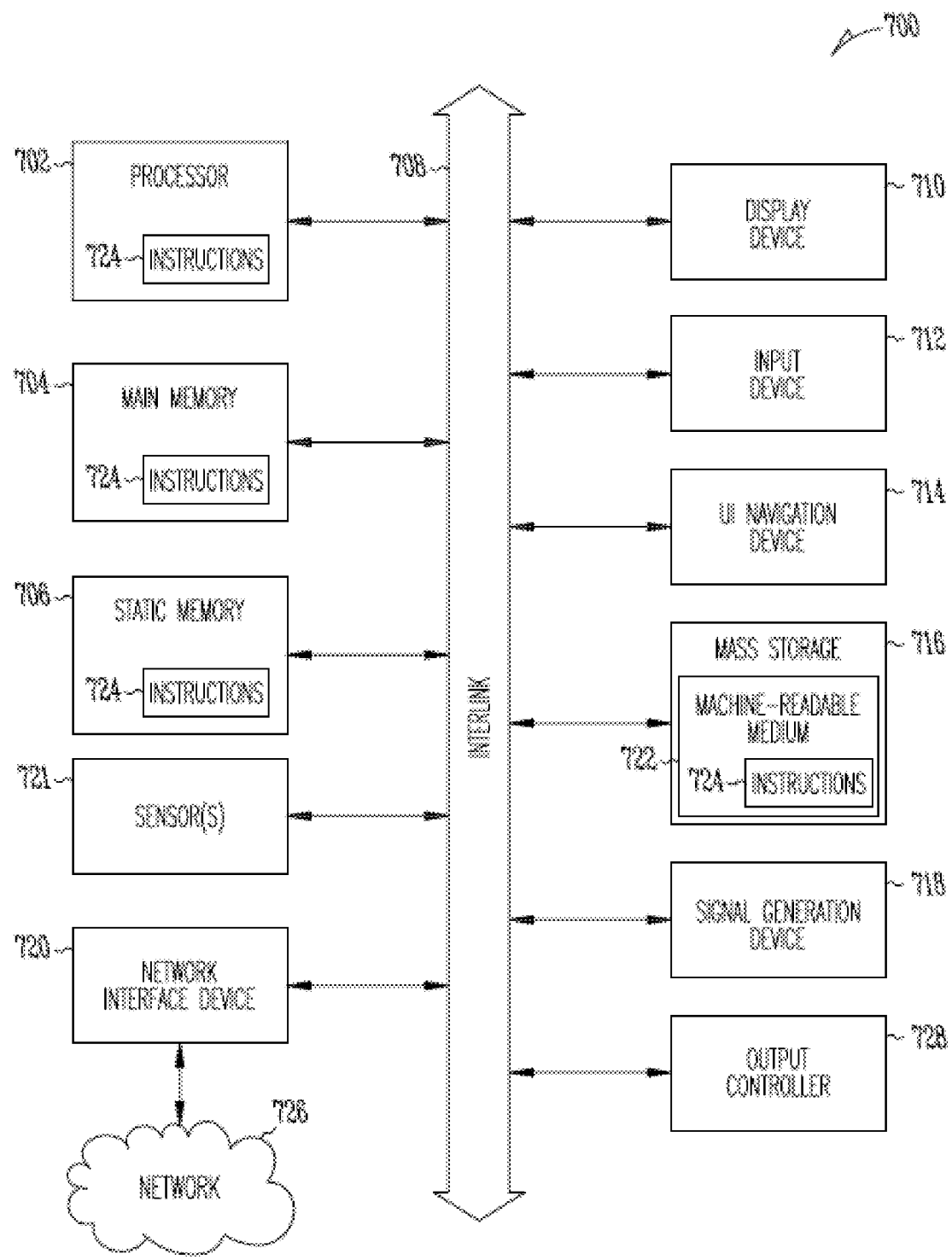
FIG. 7 illustrates generally a block diagram of an example machine upon which any one or more of the techniques (e.g., methodologies) discussed herein may perform.

FIG. 7 illustrates generally a block diagram of an example machine 700 upon which any one or more of the techniques (e.g., methodologies) discussed herein may perform. Portions of this description may apply to the computing framework of various portions of the LCP device, the IMD, or the external programmer.

In alternative embodiments, the machine 700 may operate as a standalone device or may be connected (e.g., networked) to other machines. In a networked deployment, the machine 700 may operate in the capacity of a server machine, a client machine, or both in server-client network environments. In an example, the machine 700 may act as a peer machine in peer-to-peer (P2P) (or other distributed) network environment. The machine 700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 700 may include a hardware processor 702 (e.g., a central processing unit (CPU), a graphics processing unit (GPU), a hardware processor core, or any combination thereof), a main memory 704 and a static memory 706, some or all of which may communicate with each other via an interlink (e.g., bus) 708. The machine 700 may further include a display unit 710 (e.g., a raster display, vector display, holographic display, etc.), an alphanumeric input device 712 (e.g., a keyboard), and a user interface (UI) navigation device 714 (e.g., a mouse). In an example, the display unit 710, input device 712 and UI navigation device 714 may be a touch screen display. The machine 700 may additionally include a storage device (e.g., drive unit) 716, a signal generation device 718 (e.g., a speaker), a network interface device 720, and one or more sensors 721, such as a global positioning system (GPS) sensor, compass, accelerometer, or other sensor. The machine 700 may include an output controller 728, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 716 may include a machine readable medium 722 on which is stored one or more sets of data structures or instructions 724 (e.g., software) embodying or utilized by any one or more of the techniques or functions described herein. The instructions 724 may also reside, completely or at least partially, within the main memory 704, within static memory 706, or within the hardware processor 702 during execution thereof by the machine 700. In an example, one or any combination of the hardware processor 702, the main memory 704, the static memory 706, or the storage device 716 may constitute machine-readable media.

While the machine-readable medium 722 is illustrated as a single medium, the term "machine readable medium" may include a single medium or multiple media (e.g., a centralized or distributed database, and/or associated caches and servers) configured to store the one or more instructions 724.

The term "machine readable medium" may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 724 may further be transmitted or received over a communications network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 720 may include one or more physical jacks (e.g., Ethernet, coaxial, or phone jacks) or one or more antennas to connect to the communications network 726. In an example, the network interface device 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 700, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A medical-device system for monitoring a patient at a risk of cardiac arrhythmia, comprising:
   a risk stratifier circuit configured to, in an absence of prior and present atrial arrhythmia, determine a composite risk of the patient developing a future atrial arrhythmia using a trained machine-learning model and a plurality of features of physiological information sensed via multiple sensors associated with the patient; and
   an arrhythmia monitor circuit configured to adjust an arrhythmia monitoring parameter including to selectively activate or deactivate one or more of the multiple sensors to acquire or process sensor data based at least in part on the composite risk, and to detect an atrial arrhythmia event using the adjusted arrhythmia monitoring parameter.

2. The medical-device system of claim 1, wherein the arrhythmia monitor circuit is configured to, in response to the composite risk exceeding a risk threshold, automatically adjust the arrhythmia monitoring parameter to increase a sensitivity for detecting the atrial arrhythmia event.

3. The medical-device system of claim 2, wherein the arrhythmia monitoring parameter being adjusted to increase the sensitivity for detecting the atrial arrhythmia event includes an arrhythmia detection threshold.

4. The medical-device system of claim 2, wherein the arrhythmia monitoring parameter being adjusted to increase the sensitivity for detecting the atrial arrhythmia event includes a model parameter of the trained machine-learning model.

5. The medical-device system of claim 1, comprising a sensor circuit coupled to the multiple sensors and configured to collect the physiological information from the patient in accordance with a data acquisition plan,
wherein to adjust an arrhythmia monitoring parameter, the arrhythmia monitor circuit is configured to automatically adjust the data acquisition plan based at least in part on the composite risk.

6. The medical-device system of claim 5, wherein to adjust the data acquisition plan includes to increase a data acquisition duration in response to the composite risk exceeding a risk threshold.

7. The medical-device system of claim 5, wherein to adjust the data acquisition plan includes to increase a data acquisition frequency in response to the composite risk exceeding a risk threshold.

8. The medical-device system of claim 1, wherein the risk stratifier circuit is configured to, in response to the composite risk exceeding a risk threshold, adaptively update a subsequent determination of the composite risk in the patient.

9. The medical-device system of claim 8, wherein to adaptively update the subsequent determination of the composite risk includes to update the features of physiological information being applied to the trained machine-learning model.

10. The medical-device system of claim 8, wherein to adaptively update the subsequent determination of the composite risk includes to adjust a model parameter of the trained machine-learning model.

11. The medical-device system of claim 1, comprising a model training circuit configured to generate the trained machine-learning model using physiological information sensed from a patient population.

12. The medical-device system of claim 1, wherein the plurality of features include one or more heart sound features, one or more thoracic impedance features, or one or more respiration features.

13. The medical-device system of claim 1, comprising a therapy circuit configured to generate or adjust a antiarrhythmic therapy in accordance with the composite risk.

14. A method of monitoring a patient at a risk of cardiac arrhythmia, the method comprising:
receiving physiological information sensed via multiple sensors associated with the patient;
in an absence of prior and present atrial arrhythmia, determining a composite risk of the patient developing a future atrial arrhythmia using a trained machine-learning model and a plurality of features of the received physiological information;
via an arrhythmia monitor circuit, adjusting an arrhythmia monitoring parameter including selectively activating or deactivate one or more of the multiple sensors to acquire or process sensor data based at least in part on the composite risk; and
detecting an atrial arrhythmia event using the adjusted arrhythmia monitoring parameter.

15. The method of claim 14, wherein adjusting the arrhythmia monitoring parameter includes increasing a sensitivity for detecting the atrial arrhythmia event in response to the composite risk exceeding a risk threshold.

16. The method of claim 15, wherein the arrhythmia monitoring parameter being adjusted to increase the sensitivity for detecting the atrial arrhythmia event includes at least one of an arrhythmia detection threshold or a model parameter of the trained machine-learning model.

17. The method of claim 14, wherein adjusting the arrhythmia monitoring parameter includes automatically adjusting a data acquisition plan for collecting the physiological information from the patient based at least in part on the composite risk.

18. The method of claim 17, wherein adjusting the data acquisition plan includes increasing a data acquisition duration or a data acquisition frequency in response to the composite risk exceeding a risk threshold.

19. The method of claim 14, comprising, in response to the composite risk exceeding a risk threshold, adaptively updating a subsequent determination of the composite risk in the patient, including adjusting a model parameter of the trained machine-learning model or updating the features of physiological information.

20. The method of claim 14, comprising generating or adjusting an antiarrhythmic therapy in accordance with the composite risk.

* * * * *